(12) United States Patent
Subbarayan et al.

(10) Patent No.: US 9,783,777 B1
(45) Date of Patent: Oct. 10, 2017

(54) METHOD OF MAKING THREE-DIMENSIONAL, LEAF-BASED SCAFFOLD FOR THREE-DIMENSIONAL CELL CULTURE

(71) Applicant: KING SAUD UNIVERSITY, Riyadh (SA)

(72) Inventors: Periasamy Vaiyapuri Subbarayan, Riyadh (SA); Ali Abdullah Alshatwi, Riyadh (SA); Jegan Athinarayanan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/297,096

(22) Filed: Oct. 18, 2016

(51) Int. Cl.
| | |
|---|---|
| *C08B 1/00* | (2006.01) |
| *C12N 5/00* | (2006.01) |
| *C12N 5/0775* | (2010.01) |

(52) U.S. Cl.
CPC ......... *C12N 5/0062* (2013.01); *C12N 5/0668* (2013.01); *C12N 2513/00* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 9,193,949 | B1 | 11/2015 | Alshatwi et al. |
| 2011/0274742 | A1 | 11/2011 | Arinzeh et al. |

FOREIGN PATENT DOCUMENTS

| | | |
|---|---|---|
| CN | 101979104 A | 2/2011 |
| CN | 104491926 A | 4/2015 |
| CN | 105316284 A | 2/2016 |
| CN | 105316285 A | 2/2016 |
| KR | 10-1586839 B1 | 1/2016 |

OTHER PUBLICATIONS

Reddy et al., "Properties of Ligno-cellulose Ficus religiosa Leaf Fibers", International Journal of Polymers and Technologies, 2010, 2(1), pp. 29-35.*
Whittenberger et al., "Separation and Mounting of leaf Skeletons and Epidermis", American Journal of Botany, 1948, vol. 35, No. 10, pp. 719-722.*
Bhalerao et al., "Ethenomedicinal, phytochemical and pharmacological profile of Ficus religiosa Roxb", International Journal of Current Microbiology and Applied Sciences, 2014, vol. 3, No. 11, pp. 528-538.*
Blonder, Benjamin, "How to make leaf skeletons", www.benjaminblonder.org/The secrets of leaves/making skeletons.html, Aug. 2016, pp. 1-6.*
Wayback Machine, http://www.benjaminblonder.org/The secrets of leaves/Home.html , Aug. 17, 2016, p. 1.*
Willerth, Stephanie M., and Shelly E. Sakiyama-Elbert. "Combining stem cells and biomaterial scaffolds for constructing tissues and cell delivery." (2008).

* cited by examiner

*Primary Examiner* — Laura Schuberg
(74) *Attorney, Agent, or Firm* — Richard C. Litman

(57) ABSTRACT

The method of making a three-dimensional, leaf-based scaffold for three-dimensional cell cultures includes washing a quantity of *Ficus religiosa* leaves, then treating the washed *Ficus religiosa* leaves in a sodium hydroxide solution to obtain alkali-treated *Ficus religiosa* leaves. The alkali-treated *Ficus religiosa* leaves are washed, and then superficial tissue is removed from the alkali-treated *Ficus religiosa* leaves to obtain *Ficus religiosa* leaf skeletons. The *Ficus religiosa* leaf skeletons are dried and then consecutively immersed in distilled water, a phosphate buffer saline solution, and plain Dulbecco's modified Eagle's medium (DMEM) to form the three-dimensional scaffolds for three-dimensional cell cultures. Each three-dimensional scaffold can be used for growing three-dimensional cell cultures, such as human mesenchymal stem cell cultures.

5 Claims, 8 Drawing Sheets

METHOD OF MAKING THREE-DIMENSIONAL, LEAF-BASED SCAFFOLD FOR THREE-DIMENSIONAL CELL CULTURE

BACKGROUND OF THE INVENTION

1. Field of the Invention

The present invention relates to the formation of a three-dimensional, biocompatible scaffold, and particularly to a method of making a three-dimensional scaffold from the leaves of the *Ficus religiosa*.

2. Description of the Related Art

Three-dimensional cell culture matrices, typically referred to as "scaffolds", are of great interest for culturing and growing cells. Three-dimensional cellular scaffolds show great promise in overcoming a wide variety of disadvantages found in conventional two-dimensional cell cultures, including enhancements in cell proliferation, differentiation, organization and mechanical support. A wide variety of three-dimensional scaffolds have been fabricated based on bio-mimicking of native extra cellular matrices.

Common materials used for three-dimensional culture models are typically derived from various natural or synthetic sources, such as polymers, polyethylene glycol, inorganic composites, chitosan, collagen, alginate, organic hydrogels and nanofibers. These materials, however, often suffer from a lack of multiple-functionalization, limited surface modification, poor mechanical strength, chemical hydrolysis, lack of biocompatibility, insensitivity to enzymatic processes, lack of cell specificity, biodegradability, and/or limited processability.

Thus, a method of making a three-dimensional, leaf-based scaffold for three-dimensional cell cultures solving the aforementioned problems is desired.

SUMMARY OF THE INVENTION

In a method of making a three-dimensional, leaf-based scaffold for three-dimensional cell cultures, the leaves of *Ficus religiosa* are used to produce three-dimensional scaffolds. The *Ficus religiosa* is a species of fig, variously known as the bodhi tree, the pippala tree, the peepal tree or the ashwattha tree. In order to make the three-dimensional scaffold, a quantity of *Ficus religiosa* leaves are first washed. The washed *Ficus religiosa* leaves are then treated in a sodium hydroxide solution to obtain alkali-treated *Ficus religiosa* leaves. The alkali-treated *Ficus religiosa* leaves are washed, and then superficial tissue is removed from the alkali-treated *Ficus religiosa* leaves to obtain *Ficus religiosa* leaf skeletons. The *Ficus religiosa* leaf skeletons are dried and then consecutively immersed in distilled water, a phosphate buffer saline solution, and plain Dulbecco's modified Eagle's medium (DMEM) to form the three-dimensional scaffolds for three-dimensional cell cultures. Each three-dimensional scaffold can be used for growing three-dimensional cell cultures, such as human mesenchymal stem cell cultures.

These and other features of the present invention will become readily apparent upon further review of the following specification.

cultured and grown on the three-dimensional, leaf-based scaffold for a period of 15 days.

Figure 4A:
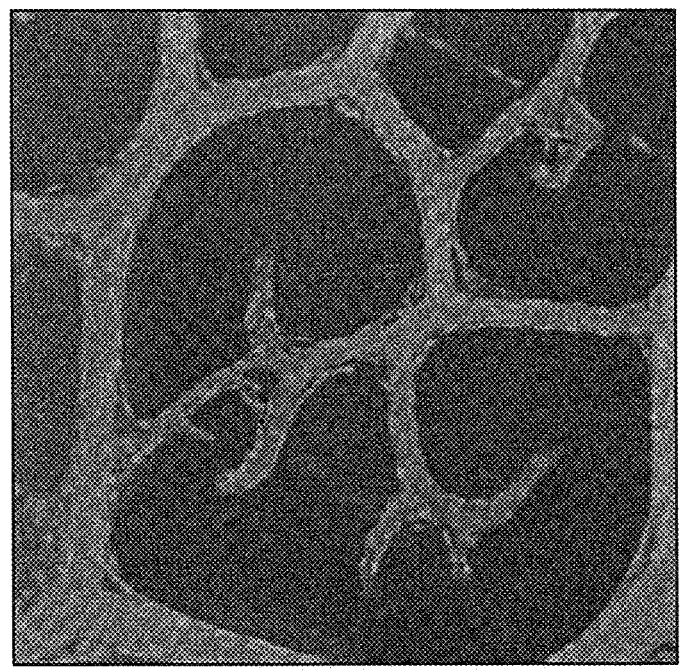
FIG. 4A is a fluorescent microscope image of a *Ficus religiosa* leaf skeleton prepared using the method of making a three-dimensional, leaf-based scaffold for three-dimensional cell cultures, stained with AO/EB (live and dead cell staining) with human mesenchymal stem cells (hMSCs) cultured and grown on the three-dimensional, leaf-based scaffold for a period of 5 days.
Figure 4B:
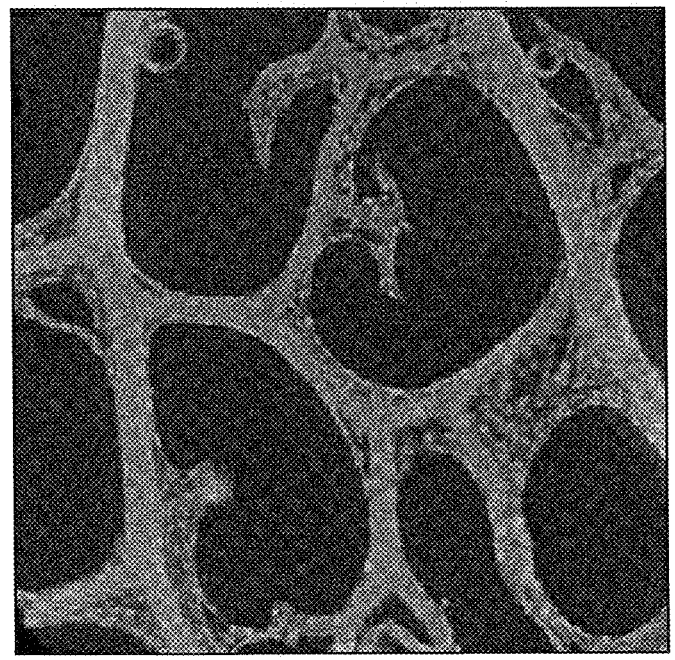
FIG. 4B is a fluorescent microscope image of a *Ficus religiosa* leaf skeleton prepared using the method of making a three-dimensional, leaf-based scaffold for three-dimensional cell cultures, stained with AO/EB (live and dead cell staining) with human mesenchymal stem cells (hMSCs) cultured and grown on the three-dimensional, leaf-based scaffold for a period of 10 days.
Figure 4C:
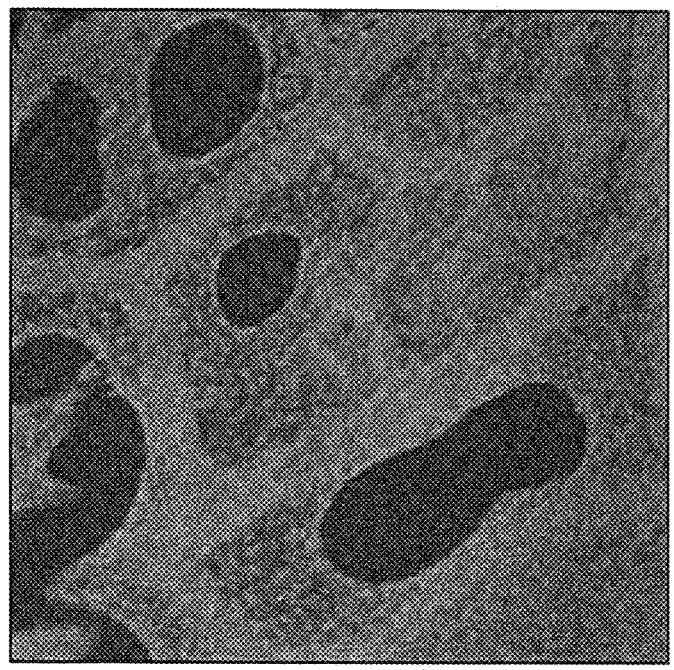
FIG. 4C is a fluorescent microscope image of a *Ficus religiosa* leaf skeleton prepared using the method of making a three-dimensional, leaf-based scaffold for three-dimensional cell cultures, stained with AO/EB (live and dead cell staining) with human mesenchymal stem cells (hMSCs)
Figure 4D:
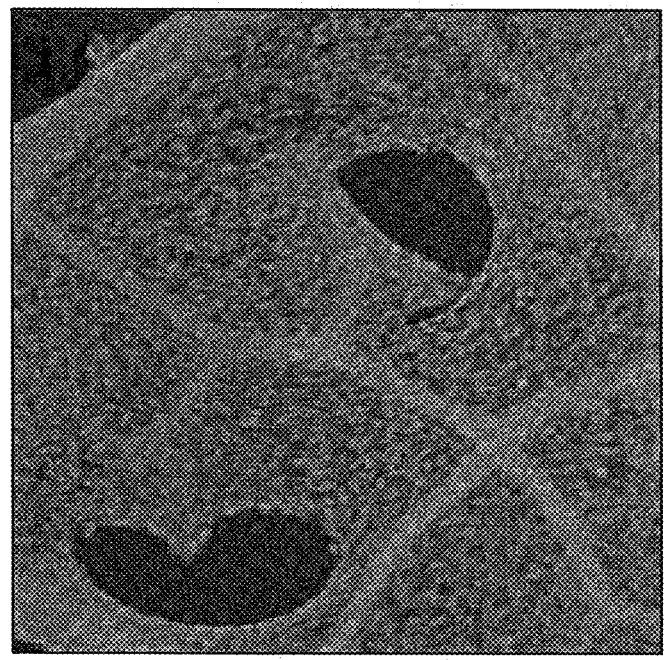

FIG. 4D is a fluorescent microscope image of a *Ficus religiosa* leaf skeleton prepared using the method of making a three-dimensional, leaf-based scaffold for three-dimensional cell cultures, stained with AO/EB (live and dead cell staining) with human mesenchymal stem cells (hMSCs) cultured and grown on the three-dimensional, leaf-based scaffold for a period of 18 days.

Figure 5A:
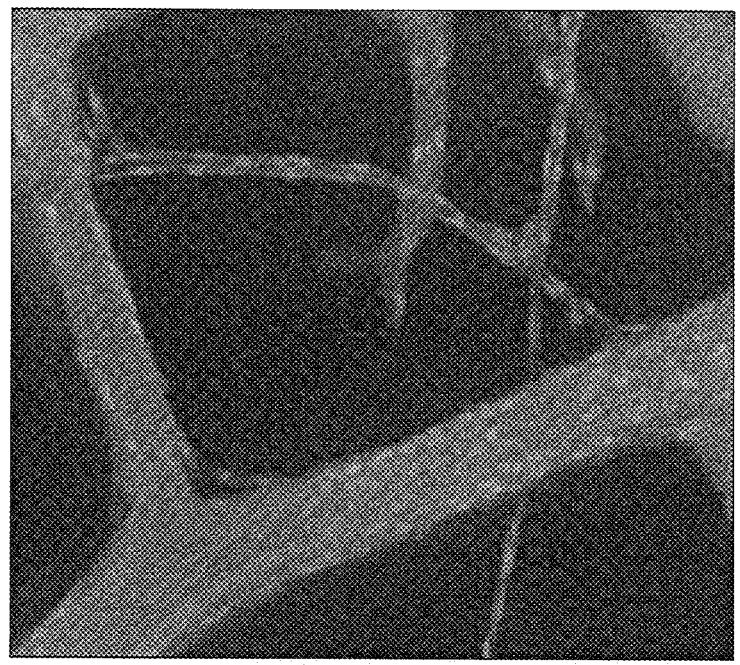

FIG. 5A is a fluorescent microscope image of a *Ficus religiosa* leaf skeleton prepared using the method of making a three-dimensional, leaf-based scaffold for three-dimensional cell cultures, stained with AO/EB staining, with human mesenchymal stem cells (hMSCs) cultured and grown on the three-dimensional, specifically showing polarization.

Figure 5B:
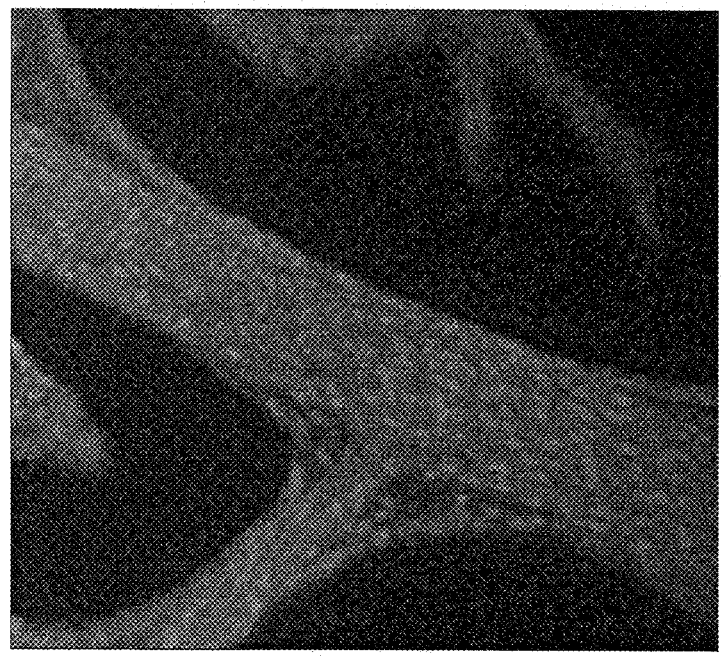

FIG. 5B is a fluorescent microscope image of a *Ficus religiosa* leaf skeleton prepared using the method of making a three-dimensional, leaf-based scaffold for three-dimensional cell cultures, stained with AO/EB staining, with human mesenchymal stem cells (hMSCs) cultured and grown on the three-dimensional, specifically showing attachment of the stem cells to the leaf skeleton.

Unless otherwise indicated, similar reference characters denote corresponding features consistently throughout the attached drawings.

DETAILED DESCRIPTION OF THE PREFERRED EMBODIMENTS

A method of making a three-dimensional, leaf-based scaffold for three-dimensional cell cultures includes treating *Ficus religiosa* leaves to provide *Ficus religiosa* leaf skeletons which can be used as three-dimensional scaffolds. The *Ficus religiosa* is a species of fig, variously known as the bodhi tree, the pippala tree, the peepal tree or the ashwattha tree. In order to make the three-dimensional scaffold, a quantity of *Ficus religiosa* leaves are first collected and washed. Washing may be performed with tap water or the like to remove any unwanted fine sands and/or dust materials.

The washed *Ficus religiosa* leaves are then treated in a sodium hydroxide solution to obtain alkali-treated *Ficus religiosa* leaves. In experiments, about 25 g of whole leaves were immersed in 1 L of a 4.0 vol % aqueous sodium hydroxide solution. The immersed leaves were kept in an autoclave at a temperature of approximately 120° C. for approximately 60 minutes under a pressure of approximately 15 lbs. The alkali-treated *Ficus religiosa* leaves were then washed with distilled water, and then superficial tissue was removed from the alkali-treated *Ficus religiosa* leaves to obtain *Ficus religiosa* leaf skeletons. In order to remove the superficial tissue, the washed, alkali-treated leaves were treated with a smooth brush, first to rupture their outer waxy layers, and then to remove the superficial layers until only the leaf skeletons remained.

The remaining *Ficus religiosa* leaf skeletons were dried in a hot air oven at approximately 50° C. for approximately 30 minutes. The dried leaf skeleton samples were then consecutively immersed in distilled water, a phosphate buffer saline solution, and plain Dulbecco's modified Eagle's medium (DMEM) to form the three-dimensional scaffolds for three-dimensional cell cultures. Immersion in each of the distilled water, phosphate buffer saline solution, and plain Dulbecco's modified Eagle's medium (DMEM) occurred under pressurized conditions at 120° C. for 20 minutes. As will be discussed in detail below, the content of cellulose, lignin, hemicellulose and ash in the treated leaf skeletons were each analyzed. The leaf skeleton structure and morphology was further assessed using light microscopy and scanning electron microscopy. Functional groups of the leaf skeleton were identified by using Fourier transform-infrared (FT-IR) spectroscopy. The crystalline nature of the plant leaf skeleton was analyzed using X-ray diffraction.

Each three-dimensional scaffold can be used for growing three-dimensional cell cultures, such as human mesenchymal stem cell cultures. In experiments, human mesenchymal stem cells (hMSC) were grown in Eagle's minimum essential medium (EMEM) with supplementation of 10% fetal bovine serum (FBS), 100 U/mL of penicillin and 100 μg/mL of streptomycin. Non-adherent and adherent cell culture plates with 30 mm and 60 mm diameter wells were used for three-dimensional cell cultures of hMSC. 3 mL of EMEM was poured in the 60 mm diameter plates and sterilized plant leaf skeleton were immersed therein. Subsequently, hMSCs were seeded at a density of $4\times10^6$ cells per plate. The plates were kept in an incubator at 37° C. with 5% $CO^2$. Three-dimensional culture growth was monitored every day and fresh media was replenished every three days.

The three-dimensional growth of hMSCs was assessed by microscopic observation. The three-dimensional cell cultures were observed using bright field, phase contrast and fluorescent microscopy. The hMSCs were seeded in 30 mm non-adherent plates for culturing on leaf skeleton surfaces for long-term periods. At two day intervals, the three-dimensional cultures were stained with AO/EB at 37° C. for 10 minutes. These stained three-dimensional cultures were examined in an inverted fluorescence microscope. The size, shape, adherence and migration of hMSCs were compared with each three-dimensional cultured construct for 21 days. The data presented below are representative of those obtained in at least three independent experiments conducted in triplicate.

As shown below in Table 1, the chemical analysis of the plant leaves and their skeletons indicates that each contains cellulose, lignin, hemicellulose and ash. The results indicate that the alkali-treated leaf skeletons produced by the present inventive method contain high quantities of cellulose (53.7%) and lignin (36.1%), and low quantities of hemicellulose and silica. The alkali treatment process significantly eliminates hemicellulose and slightly removes lignin from *Ficus religiosa* leaf.

TABLE 1

Chemical Composition of *Ficus Religiosa* Leaves and Skeletons

| Components | Leaf Composition (%) | Skeleton Composition (%) |
| --- | --- | --- |
| Lignin | 26.6 | 36.1 |
| Cellulose | 41.2 | 53.7 |
| Hemicellulose | 31.0 | 9.2 |
| Silica | 1.2 | 1.0 |

Figure 1:
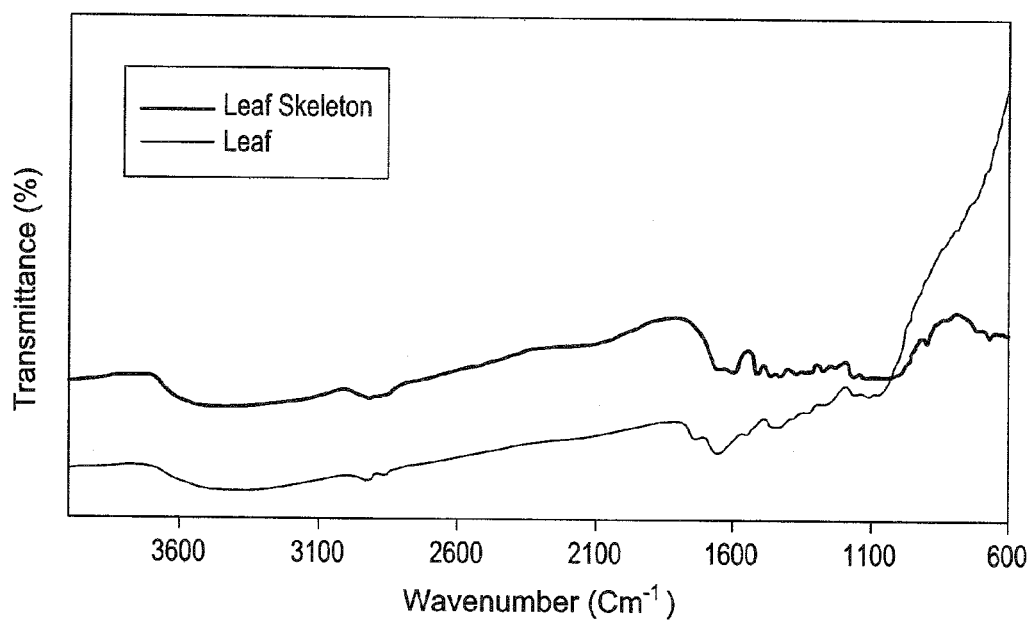
FIG. 1 is a graph showing Fourier transform infrared spectroscopy (FT-IR) results of a *Ficus religiosa* leaf and a leaf skeleton of the *Ficus religiosa* leaf prepared using the method of making a three-dimensional, leaf-based scaffold for three-dimensional cell cultures according to the present invention.

FIG. 1 shows the results of the FT-IR analysis of the alkali-treated leaf skeletons, specifically showing well-defined characteristic absorption peaks at 3445, 1509, 1459, 1373, 1270, 1061 and 896 $cm^{-1}$. The FT-IR results indicate that the alkali-treated leaf skeletons contain α-cellulose, hemicellulose and lignin. In the full, untreated leaf samples, additional bands are seen at 1740 and 1270 $cm^{-1}$, which correspond to hemicellulose. However, these peaks are absent in the alkali-treated leaf skeletons, thus indicating hemicellulose elimination. The bands at around 3445 cm$^{-1}$ correspond to α-cellulose, whereas the remaining bands belong to lignin. Energy-dispersive X-ray spectroscopy (EDX) patterns of alkali-treated leaf skeletons showed peaks corresponding to C, O, Si and Na. Thus, it was determined that the leaf skeleton samples contained cellulose, lignin, hemicellulose and silica.

Figure 2A:
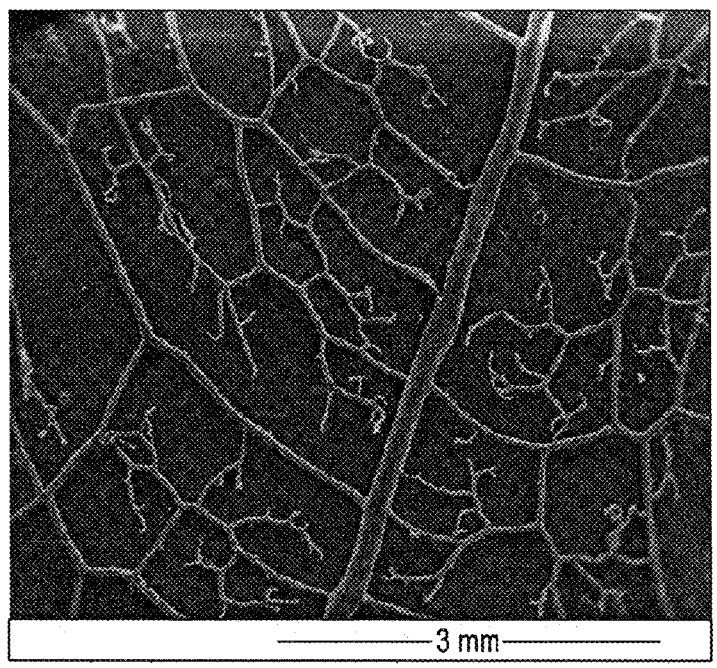
FIG. 2A is a scanning electron microscope (SEM) image of a *Ficus religiosa* leaf skeleton prepared using the method of making a three-dimensional, leaf-based scaffold for three-dimensional cell cultures, at a magnification on the order of 3 mm.
Figure 2B:
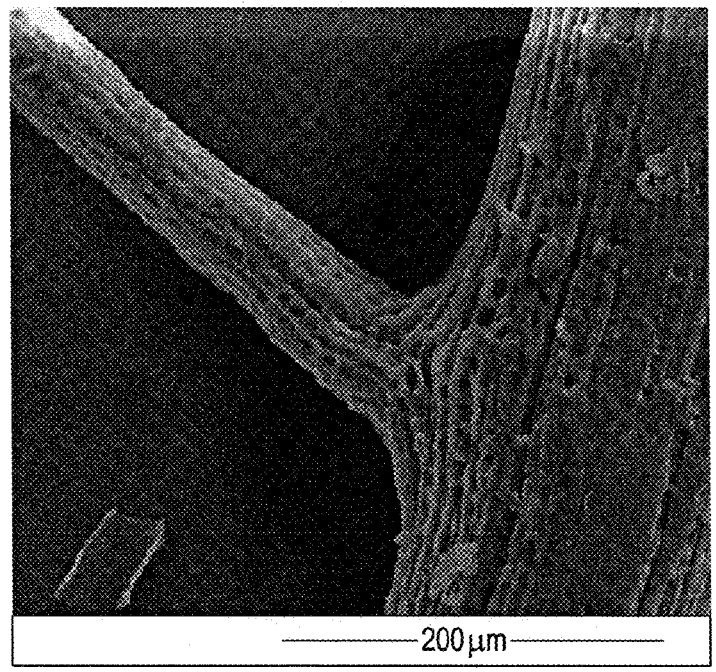
FIG. 2B is a scanning electron microscope (SEM) image of a *Ficus religiosa* leaf skeleton prepared using the method of making a three-dimensional, leaf-based scaffold for three-dimensional cell cultures, at a magnification on the order of 200 μm.
Figure 2C:
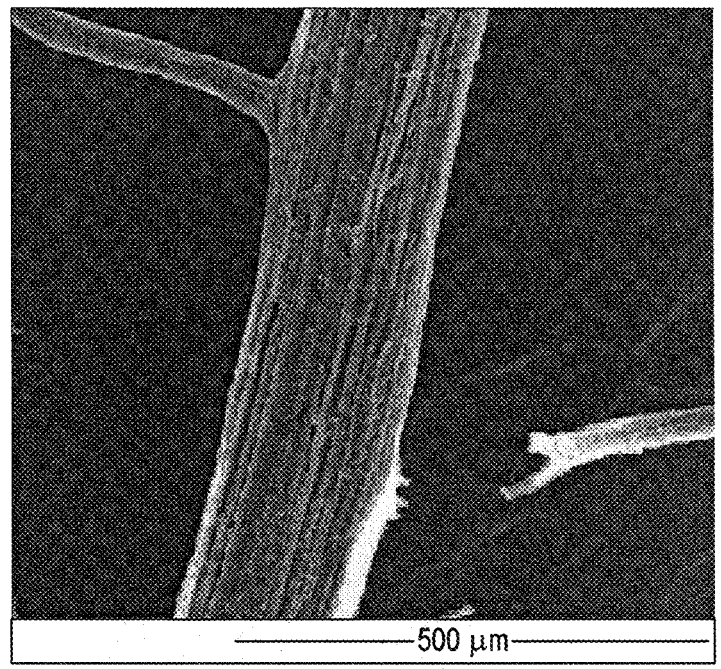
FIG. 2C is a scanning electron microscope (SEM) image of a *Ficus religiosa* leaf skeleton prepared using the method of making a three-dimensional, leaf-based scaffold for three-dimensional cell cultures, at a magnification on the order of 500 μm.
Figure 2D:
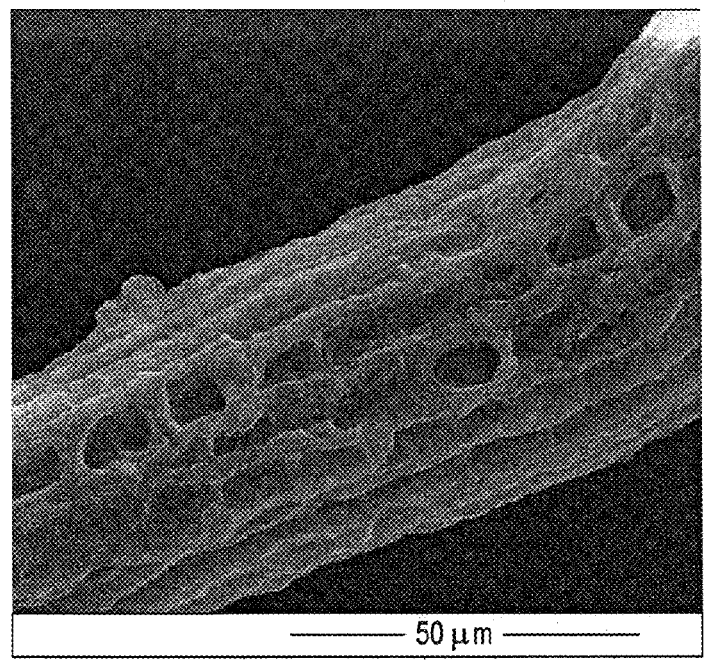
FIG. 2D is a scanning electron microscope (SEM) image of a *Ficus religiosa* leaf skeleton prepared using the method of making a three-dimensional, leaf-based scaffold for three-dimensional cell cultures, at a magnification on the order of 50 μm.
Figure 3A:
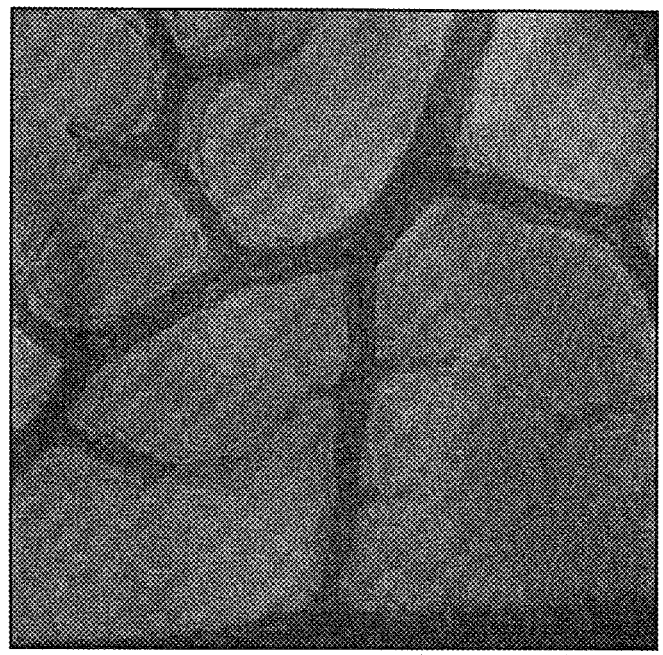
FIG. 3A is a bright field microscope image of a stained *Ficus religiosa* leaf skeleton prepared using the method of making a three-dimensional, leaf-based scaffold for three-dimensional cell cultures with human mesenchymal stem cells (hMSCs) cultured and grown on the three-dimensional, leaf-based scaffold for a period of 5 days.
Figure 3B:
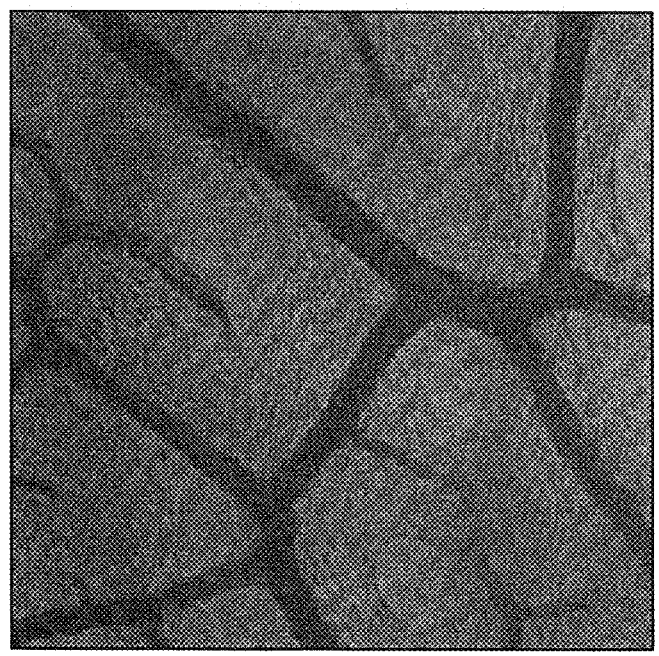
FIG. 3B is a bright field microscope image of a stained *Ficus religiosa* leaf skeleton prepared using the method of making a three-dimensional, leaf-based scaffold for three-dimensional cell cultures with human mesenchymal stem cells (hMSCs) cultured and grown on the three-dimensional, leaf-based scaffold for a period of 10 days.
Figure 3C:
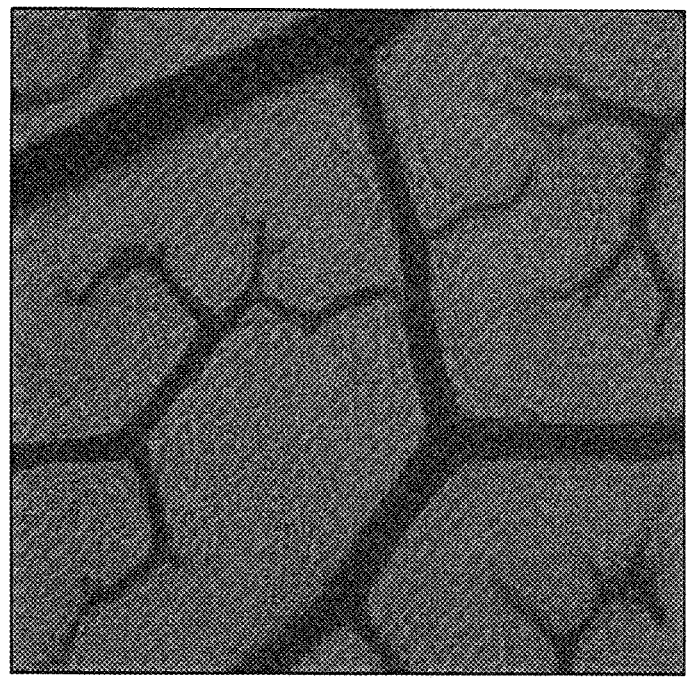
FIG. 3C is a bright field microscope image of a stained *Ficus religiosa* leaf skeleton prepared using the method of making a three-dimensional, leaf-based scaffold for three-dimensional cell cultures with human mesenchymal stem cells (hMSCs) cultured and grown on the three-dimensional, leaf-based scaffold for a period of 15 days.
Figure 3D:
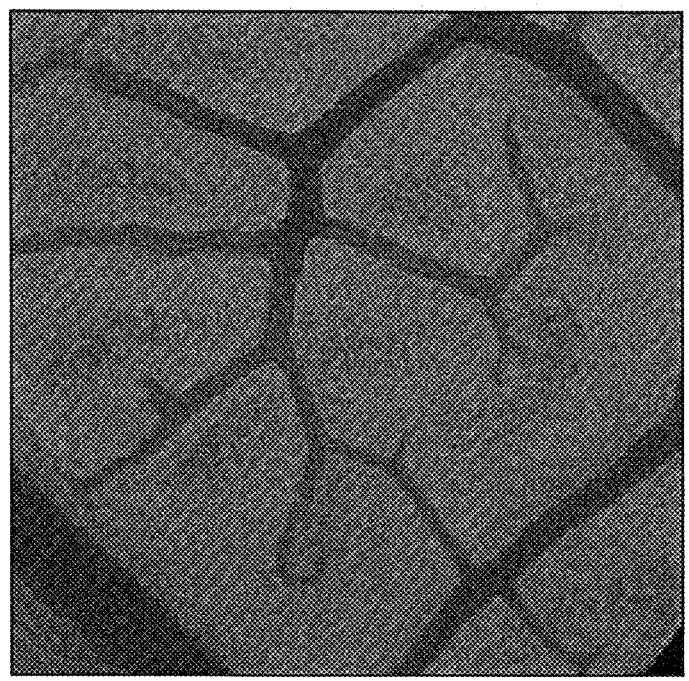
FIG. 3D is a bright field microscope image of a stained *Ficus religiosa* leaf skeleton prepared using the method of making a three-dimensional, leaf-based scaffold for three-dimensional cell cultures with human mesenchymal stem cells (hMSCs) cultured and grown on the three-dimensional, leaf-based scaffold for a period of 18 days.

Scanning electron microscopy (SEM) images show the surface morphology and architecture of the plant leaf skeletons. Low magnification of leaf skeleton SEM images suggested a plant leaf skeleton architecture with venation (shown in FIG. 2A). At high magnification, SEM images indicate that the alkali-treated plant leaf skeletons have a microporous surface topography (FIG. 2B). Moreover, the alkali-treated leaf skeletons are rough and the fibers have a multicellular structure (FIG. 2C). Each unit cell of fibers is composed of small particles of cellulose surrounded by, and cemented together with, lignin and hemicellulose. Square-shape compartments are observed on the surface of the plant leaf skeleton architecture, as shown in FIG. 2D.

The plant leaf skeleton biocompatible properties were assessed using the AO/EB staining method. The results are illustrated in FIGS. 3A-3D, respectively showing cultures at 5 days, 10 days, 15 days and 18 days. FIGS. 3A-3D indicate that the plant leaf skeletons show excellent biocompatibility. Furthermore, hMSCs were cultured on the three-dimensional plant leaf skeleton surfaces for 21 days and cell viability was assessed. The cell viability increased with an increase in the incubation time, thus indicating that the plant leaf skeleton enhances the cell attachment and proliferation of hMSCs. The results clearly suggest that the plant leaf skeletons are suitable for three-dimensional cell cultures.

The cellular and nuclear morphological changes were assessed using bright field and fluorescence microscopy. The bright field microscopic images illustrated the presence of healthy cells with layered flattened structures (FIGS. 3A-3D). The hMSCs attached and spread over the surfaces of the leaf architectures. The alkali-treated leaf architectures were fully covered with the hMSCs at 18 days of incubation. The cells proliferated on the leaf skeleton surfaces and cell numbers increased with incubation time. The bright field microscopic images indicate that the plant leaf skeleton has a microporous surface topography, which improves the hMSCs attachment and growth. The results show that the leaf skeleton-based scaffolds are suitable for differentiation of hMSCs into various lineages, such as chondrocytes, neural cells, myocytes, osteoblasts and adipocytes.

Nuclear morphological changes were assessed using AO/EB staining. A monolayer of green fluorescent cells with intact nuclei was observed on the surface of the plant leaf scaffold. The results indicated no significant changes observed in the nuclear morphology of the layered structure of hMSCs on plant leaf skeleton architecture for 1 to 21 days. This can be seen in FIGS. 4A-4D, respectively showing cultures at 5 days, 10 days, 15 days and 18 days. Additionally, FIG. 5A shows polarization in hMSCs on the leaf skeleton surfaces, and FIG. 5B shows hMSC attachment on the leaf skeleton surfaces. The density of cells, colony of cells and area of cells increased on the plant leaf architecture with an increase in the incubation time. This suggests that the leaf skeleton's microporous structure enhances cell attachment and proliferation. Moreover, the scaffold's inner microchannals transport oxygen and nutrients. The scaffold may be a suitable platform for a multi-layer cell culture, a cell-based assay model, high-throughput drug screening, cell-replacement therapy, stem cell differentiation and large scale cell, production for tissue engineering applications.

It is to be understood that the present invention is not limited to the embodiments described above, but encompasses any and all embodiments within the scope of the following claims.

We claim:

1. A method of making a three-dimensional, leaf-based scaffold for three-dimensional cell cultures, comprising the steps of:
    treating *Ficus religiosa* leaves in a sodium hydroxide solution to obtain alkali-treated *Ficus religiosa* leaves;
    washing the alkali-treated *Ficus religiosa* leaves;
    removing layers of superficial tissue from the alkali-treated *Ficus religiosa* leaves to obtain *Ficus religiosa* leaf skeletons;
    drying the *Ficus religiosa* leaf skeletons to obtain dried *Ficus religiosa* leaf skeletons; and
    immersing the dried *Ficus religiosa* leaf skeletons in a cell culture medium to provide a three-dimensional, leaf-based scaffold for three-dimensional cell cultures, wherein the cell culture medium is Dulbecco's modified Eagle's medium (DMEM).

2. The method of making a three-dimensional, leaf-based scaffold for three-dimensional cell cultures as recited in claim 1, wherein the sodium hydroxide solution comprises in a 4.0 vol % aqueous solution of sodium hydroxide.

3. The method of making a three-dimensional, leaf-based scaffold for three-dimensional cell cultures as recited in claim 2, further comprising heating the washed *Ficus religiosa* leaves at a temperature of approximately 120° C. for approximately 60 minutes under a pressure of approximately 15 lbs.

4. The method of making a three-dimensional, leaf-based scaffold for three-dimensional cell cultures as recited in claim 1, wherein the step of drying the *Ficus religiosa* leaf skeletons comprises drying the *Ficus religiosa* leaf skeletons at a temperature of approximately 50° C. for approximately 30 minutes.

5. The method of making a three-dimensional, leaf-based scaffold for three-dimensional cell cultures as recited in claim 1, further comprising:
    consecutively immersing the dried *Ficus religiosa* leaf skeletons in distilled water and a phosphate buffer saline solution, prior to the step of immersing the dried *Ficus religiosa* leaf skeletons in the cell culture medium.

* * * * *